(12) United States Patent
Watling

(10) Patent No.: US 7,186,371 B1
(45) Date of Patent: *Mar. 6, 2007

(54) SEALED ENCLOSURE STERILIZATION

(75) Inventor: David Watling, Westcott (GB)

(73) Assignee: Bioquell UK Limited., Andover (GB)

( * ) Notice: Subject to any disclaimer, the term of this patent is extended or adjusted under 35 U.S.C. 154(b) by 671 days.

This patent is subject to a terminal disclaimer.

(21) Appl. No.: 10/009,102

(22) PCT Filed: Jun. 2, 2000

(86) PCT No.: PCT/GB00/02137

§ 371 (c)(1),
(2), (4) Date: Mar. 6, 2002

(87) PCT Pub. No.: WO00/74734

PCT Pub. Date: Dec. 14, 2000

(30) Foreign Application Priority Data

Jun. 4, 1999 (GB) .................................. 9913082.5

(51) Int. Cl.
*A61L 2/00* (2006.01)

(52) U.S. Cl. ............................... 422/3; 422/28; 422/33; 422/292; 422/295; 422/298; 422/305; 422/306

(58) Field of Classification Search ................ 422/298, 422/295, 292, 305, 306, 1, 3, 28, 33, 120, 422/122

See application file for complete search history.

(56) References Cited

U.S. PATENT DOCUMENTS

| | | | | |
|---|---|---|---|---|
| 4,512,951 A | * | 4/1985 | Koubek | 422/33 |
| 4,631,173 A | | 12/1986 | Müller et al. | |
| 4,742,667 A | | 5/1988 | Müller et al. | |
| 4,797,255 A | * | 1/1989 | Hatanaka et al. | 422/28 |
| 4,909,999 A | * | 3/1990 | Cummings et al. | 422/298 |
| 4,952,370 A | | 8/1990 | Cummings et al. | |
| 5,173,258 A | * | 12/1992 | Childers | 422/27 |
| 5,173,259 A | * | 12/1992 | Bordini | 422/28 |
| 5,229,071 A | * | 7/1993 | Meo, III | 422/2 |
| 5,525,295 A | * | 6/1996 | Pflug et al. | 422/27 |
| 5,906,794 A | * | 5/1999 | Childers | 422/28 |
| 7,014,813 B1 | * | 3/2006 | Watling et al. | 422/26 |

(Continued)

FOREIGN PATENT DOCUMENTS

DE 44 27 577 A1 2/1996

(Continued)

*Primary Examiner*—Krisanne Jastrzab
(74) *Attorney, Agent, or Firm*—Workman Nydegger

(57) ABSTRACT

An apparatus for sterilizing a sealed enclosure (1) includes a fan (8) for circulating a gas through a preparation circuit (11) and through the enclosure. The preparation circuit includes an evaporation chamber (10) for dispensing a decontaminant gas and water vapor mixture into the circulating gas to flow therewith through the enclosure and to reach a concentration in the enclosure above the dew point for the ambient temperature in the enclosure and thereby to condense onto surfaces in the enclosure to sterilize such surfaces. A monitor (15) measures gas temperature and dew point/condensation are monitored (17, 18) in the enclosure. The resulting signals led to a control module (19) for controlling the rate of dispensing of the decontaminant gas and water vapor into the gas in the preparation circuit in response to the levels determined by said monitoring to provide a required level of condensation of the decontaminant gas and water vapor in the enclosure.

17 Claims, 1 Drawing Sheet

Figure 1:
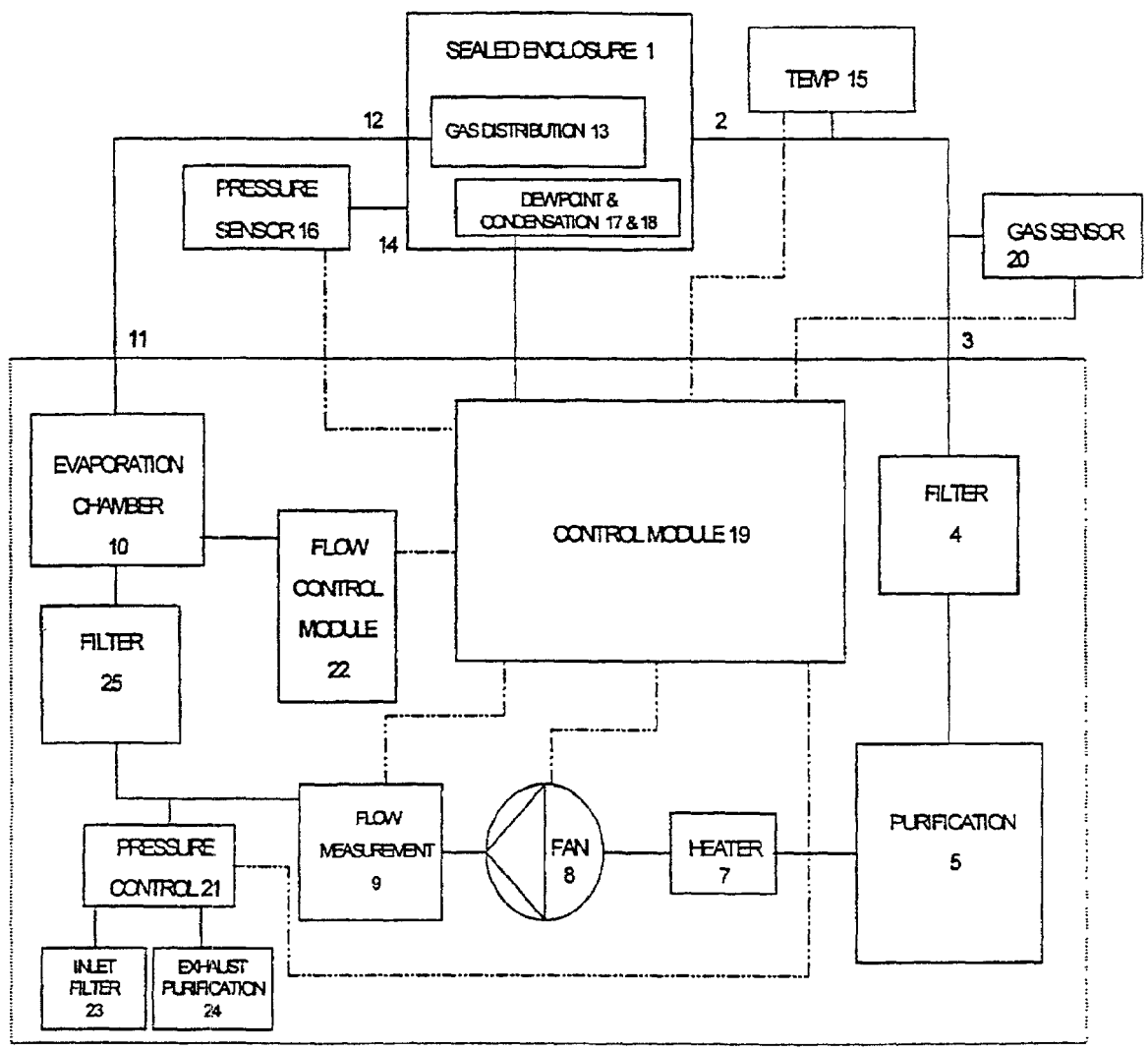

U.S. PATENT DOCUMENTS 7,025,932 B2 * 4/2006 Martin et al. .................. 422/3

FOREIGN PATENT DOCUMENTS

| | | |
|---|---|---|
| EP | 0 486 623 B1 | 1/1997 |
| EP | 0 880 972 A2 | 12/1998 |
| GB | 2 217 619 A | 11/1989 |
| GB | 2 308 066 A | 6/1997 |
| JP | 1-17936 | 11/1983 |
| JP | 61-4543 | 4/1984 |
| JP | 7-163639 | 6/1995 |
| JP | 10-328276 | 12/1998 |
| JP | 2000-513247 | 10/2000 |
| JP | 2002-504005 | 2/2002 |
| WO | WO 86/04698 | 8/1986 |
| WO | WO 89/06140 | 7/1989 |
| WO | WO 91/05573 | 5/1991 |
| WO | WO 97/47331 | 12/1997 |
| WO | WO 98/57673 | 12/1998 |
| WO | WO 99/30747 | 6/1999 |

* cited by examiner

SEALED ENCLOSURE STERILIZATION

The present invention relates to decontamination and sterilisation systems and more particularly to the control of gaseous decontamination and systems where the vapour has more than one component.

Conventional gas sterilisation and decontamination systems have been designed in order to avoid condensation, and as such both flow through and recirculating systems have been so organised as to keep the vapour concentrations, especially of water, below the dew point. Examples of such systems are described in European Patent EP0486623B1, UK Patent 2 217 619 B, WO 89/06140 and UK Patent application GB 2308 066 A.

More recent work has shown that for rapid surface sterilisation and decontamination in rooms and smaller chambers, or isolators, condensation of a mixture of vapours of a gaseous decontaminant such as hydrogen peroxide and water is essential.

The object of the present invention is to control the sterilisation and decontamination systems both for closed recirculating systems, flow through systems and systems which use recirculation with a proportion of the recirculation air or air/gas mixture being exhausted from the closed system so that condensation may occur rapidly, evenly and controllable through the area to be sterilised or decontaminated.

For the purpose of this patent the term decontaminate shall in future include both chemical and microbiological decontamination. Microbiological decontamination shall mean the reduction of the viable bioburden, which is generally described either as sterilisation, sanitation or disinfection.

This invention provides a method of sterilizing a sealed enclosure comprising the steps of: circulating the gas through the enclosure, and through a preparation region, in the preparation region dispensing a decontaminant gas and water vapour mixture into the circulating gas to flow therewith through the enclosure to reach a concentration in the enclosure above the dew point for the ambient temperature in the chamber and thereby to condense onto surfaces in the enclosure to sterilise such surfaces; wherein the gas temperature and the condensation of the decontaminant gas in the enclosure are monitored and the dispensing of the decontaminant gas and water vapour into the gas in the preparation region is controlled in response to the levels determined by said monitoring to provide a requisite level of condensation of the decontaminant gas/water vapour in the enclosure.

The term "sealed enclosure" shall include any chamber or room that may for practical purposes be sealed so as to prevent the escape of such amounts of active gas as to cause a hazard.

The sealed enclosure is connected to a means of processing by two pipes through which air or a mixture of air and gases, where the gases are hydrogen peroxide and water vapour, may circulate. The air or mixture of air and gases being delivered from the means of processing to the sealed enclosure to then be returned to the processing means or alternatively a flow through system where the air or air/gas mixture is vented from the sealed enclosure in a safe manner. The air or mixture of air and gases on entering the means of processing may, if necessary, first pass through a system of purification to remove and make safe any gases within the mixture of air and gases. This purification process will not normally be required because of the stability of the gas mixture. Hydrogen peroxide gas has been shown to be stable in the homogenous vapour phase at ambient and temperatures below 300° C. Decomposition will occur on surfaces but only at insignificant rates on those surfaces generally found in clean rooms and isolators. High rates of decomposition will occur on certain organic substances such as micro-organisms but as the quantity of these materials is very small the total amount of decomposition is also very small, and hence does not significantly affect the gas concentration. A fan or pump or compressor is then used to propel the air or mixture of air and gases around the system, and drive the fluid through the evaporation chamber where additional gases are added to the air or air gas mixture. The enriched air/gas mixture is then passed through the connection from the processing means to the sealed chamber.

The function of the air/gas mixture in the sealed chamber is to decontaminate the surfaces of the chamber.

Similar systems have been employed for some time for the surface sterilisation of sealed enclosures, but in these applications it has always been considered important to avoid condensation, Patent EP 0 486 623 B1 specifically sets out a table of operation to avoid condensation. The present invention sets out a method of decontamination by micro condensation and provides for a method of control. It has been established that faster and more reliable surface decontamination may be achieved if micro condensation is encouraged and controlled. The dew point of any hydrogen peroxide and water vapour mixture may be ascertained from the activity coefficients for the gases, and by using a combination of dew point data, the actual dew point within the sealed chamber and the temperature it is possible to calculate the concentration of hydrogen peroxide in the condensate.

A knowledge of the condensation parameters, and the amount of condensation allows a prediction of the time at which surface decontamination will occur. For such a system to function reliably it is also essential that there is very good distribution of gas within the sealed enclosure.

The active gas in such micro-condensation systems used for decontamination is not limited to hydrogen peroxide but includes a gas or mixture of gases that exhibits the correct vapour pressure characteristics.

The invention also provides an apparatus for sterilizing a sealed enclosure comprising means for circulating a gas through a preparation region and through the enclosure and means in the preparation region for dispensing a decontaminant gas and water vapour mixture into the circulating gas to flow therewith through the enclosure to reach a concentration in the enclosure above the dew point for the ambient temperature in the chamber and thereby to condense onto surfaces in the enclosure to sterilise such surfaces; wherein means are provided for monitoring the temperature and the concentration of the decontaminant gas in the enclosure and means are provided for controlling the rate of dispensing of the decontaminant gas and water vapour into the gas in the preparation region in response to the levels determined by said monitoring to provide a predetermined rate of condensation of the decontaminant gas and water vapour in the enclosure.

The following is a description of one embodiment of the invention, reference being made to the accompanying drawing which is a diagrammatic illustration of a decontamination apparatus for a sealed enclosure.

The sealed enclosure 1 is connected to a sealed outlet pipe at 2 which connects to the processing means at 3. The air or air/gas mixture then passes through a filter 4 to remove particulate contamination. As an option if it is considered that the gas mixtures may have partially decomposed in the sealed chamber the air or air/gas mixture may be passed through a purification process 5. Step 5 is only required in exceptional circumstances when significant decomposition of the active gas has taken place. This component would not normally form part of the processing means. The air or air/gas mixture should then be heated in 7 to bring it to a stable temperature before passing to the fan or pump or compressor 8 which is used to drive the air or air/gas mixture through the processing means, the connecting pipes and the sealed enclosure. The volumetric flow is then measured in 9 before the air or air gas mixture is passed to the evaporation chamber 10 where more of the gas mixture is added by evaporation of the decontamination solution on a hot surface. The air or air/gas mixture passes through a filter 25 before entering the evaporation chamber 10 to ensure that particulate matter is removed from the flow. The rate at which the liquid is fed to the evaporation chamber 10 is controlled by the Liquid Flow Module 22.

Because it may be necessary to control the pressure inside the sealed enclosure a pressure control module 21 is used to raise or lower the pressure by supply or extracting air. Any air added to the system must be filtered 23 and any air extracted must be rendered safe by the removal of any active gas either by absorbing the gas or by decomposition with a catalyst 24. The air or air/gas mixture leaves the processing means at 11 through a sealed connecting pipe and is delivered to the sealed enclosure at 12. Within the sealed enclosure is a gas distribution device 13 which generates sufficient turbulence in the air or air/gas mixture within the sealed enclosure to ensure rapid and even distribution of the air or air/gas mixture.

The gas distribution system in the simplest form would be a circulating fan mounted inside the sealed enclosure which generated sufficient turbulence in the air gas mixture to generate an even distribution of gas. A more affective technique would be to use a nozzle rotating about two axles at right angles directing a jet of gas as it is delivered to the chamber at high velocity over a fixed pattern. The use of such a rotating nozzle has the advantage of generating repeating patterns over the internal surface of the sealed chamber. It also allows the air/gas mixture to be delivered at an optimum temperature from a heated pipe 11 to 12 and by correct design of the nozzle allows the delivered gas velocity to be adjusted to suit the geometry of the chamber.

A pressure sensing point 14 on the sealed enclosure is connected by a sealed tube to the pressure sensing device at 16. The signal from the pressure sensor is transmitted to the control module 19 which in turn sends signals to the pressure control module 21 to adjust the internal pressure of the sealed enclosure. Such pressure control may be inactivated when it is not possible because of the size of construction of the sealed enclosure or when pressure control is not required. The dew point and condensation monitor 17 is connected electronically to the processing unit 18 which may be either attached to the sealed enclosure or in the processing means. The signal from the dew point and condensation processing unit is passed to the control module and is used to control the rate of micro-condensation that occurs inside the sealed enclosure. The temperature 15 of the air or the air/gas mixture either inside the sealed enclosure, or leaving the sealed enclosure, or on entering the processing means is measured and the signal passed to the control module 19. A gas sensor 20 measures the gas concentration either inside the sealed enclosure, or on leaving the sealed enclosure, or on entering the processing means. The signal from the gas sensor is transmitted electronically to the control module 19. If the distance from the processing means to the sealed enclosure is great the pipe connecting 11 to 12 should be heated and insulated to maintain the temperature above the dew point of the air/gas mixture being delivered from the evaporation chamber.

Method of Control

As the decontamination process relies on micro-condensation on particles on the surface it is important that this process is controlled. This control is achieved with reference to the dew point and rate of condensation as measured on the dew point and condensation sensor 17 together with the temperature sensor 15 and the gas sensor 20.

After an initial stabilisation period during which the air flow and temperature are stabilised, the liquid flow module 22, under the direction of the control module 19 will start to dispense a measured flow of liquid to the evaporation chamber 10. This measure flow of liquid will be turned into a gas mixture in the evaporation chamber and mixed with a measured flow of air as measured by the flow measurement device 9 and controlled via the control module 19 by the fan or pump or compressor 8.

This technique will provide a predetermined air gas mixture concentration which will be delivered to the sealed enclosure 1 and evenly distributed throughout the chamber by the distribution device 13. This air/gas mixture must have a concentration above the dew point for the temperature of the sealed enclosure 1. Once sufficient air/gas mixture has circulated round the system through the sealed enclosure and the processing means to raise the air/gas concentration above the dew point then the condensation will occur and be signalled by the dew point and condensation sensor 17. From a knowledge of the temperature as indicated by the temperature sensor 15 and the gas concentration as indicated by the gas sensor 20 and the dew point it is possible to derive the concentration of the steriliant in the micro-condensation. Once the dew point has been reached the rate of liquid delivered by the liquid flow module 22 to the evaporation chamber 10 will be adjusted to achieve the required rate of condensation in the sealed enclosure. After a sufficient amount of condensation has occurred as measured by the dew point and condensation sensor 17 and also by the amount of liquid delivered from the liquid flow module 22 to the evaporation chamber 10 then the liquid flow is stopped as decontamination will have been achieved. The amount of condensation in any sealed enclosure to achieve decontamination will have to be demonstrated by the use of a testing technique suitable for the containment.

Once the liquid flow from the liquid flow module 22 to the evaporation chamber 10 has been stopped then a system to remove the decontaminant gas from the sealed enclosure 1 must be operated. This may either consist of a method of passing clean filtered air through the sealed enclosure 1 and passing the air from the sealed enclosure which will then contain active gas safely to atmosphere or by circulating the air/gas mixture through an auxiliary circuit to remove the decontaminant gas. Such an auxiliary circuit could be either a catalyst decomposition device or an absorption technique such as activated carbon. It may also be possible to use a combination of both methods, first reducing the concentration with a catalyst or activated carbon and then passing the balance safely to atmosphere.

The invention claimed is:

1. A method of sterilising a sealed enclosure comprising:
   continuously recirculating a gas through the enclosure and through a preparation region for a period of time; and
   dispensing a mixture of decontaminant gas and water vapour into the recirculating gas in the preparation region to flow therewith through the enclosure to reach a concentration in the enclosure above the dew point of the gas and water vapour mixture for the ambient temperature in the chamber and thereby to condense onto surfaces in the enclosure to sterilise such surfaces; wherein the gas temperature in or exiting the enclosure or entering the preparation region, decontaminant gas concentration in or exiting the enclosure or entering the preparation region and condensation of the decontaminant gas on the surfaces of the enclosure are measured and the dispensing of the mixture of decontaminant gas and water vapour into the gas in the preparation region is controlled in response to the levels determined by said measuring to provide a requisite level of condensation of the decontaminant gas/water vapour in the enclosure.

2. A method of sterilising a sealed enclosure as claimed in claim 1, wherein the gas circulated through the enclosure is air.

3. A method as claimed in claim 1, wherein the gas is filtered in said preparation region prior to circulation through the enclosure.

4. A method as claimed in claim 2, wherein the gas is filtered in said preparation region prior to circulation through the enclosure.

5. A method of sterilising a sealed enclosure as claimed in claim 1, wherein means are provided for monitoring the gas pressure in the enclosure and means are provided for adjusting the gas pressure therein by controlling the supply of gas circulating through the enclosure.

6. A method as claimed in claim 1, wherein after a sufficient amount of decontaminant gas has been condensed in the chamber to achieve decontamination, supply of the decontaminant gas and water vapour mixture to the preparation region is terminated and the decontaminant gas is removed from the sealed enclosure.

7. A method of sterilising a sealed enclosure as claimed in claim 6, wherein the method of moving the decontaminant gas from the sealed enclosure comprises:
passing clean filtered gas through the enclosure and releasing the gas exiting the enclosure to atmosphere; or
circulating the gas exiting the enclosure through an auxiliary circuit containing a catalytic decomposition device or absorption device for the decontaminant gas to remove the decontaminant gas.

8. An apparatus for sterilising a sealed enclosure comprising:
means (8) for continuously recirculating a gas through a preparation region (3) and through the enclosure (1) for a period of time; and
means (10) in the preparation region for dispensing a mixture of decontaminant gas and water vapour mixture into the recirculating gas to flow therewith through the enclosure to reach a concentration in the enclosure above the dew point for the ambient temperature in the chamber and thereby to condense onto surfaces in the enclosure to sterilise such surfaces,
wherein means (15) are provided for measuring gas temperature in or exiting the enclosure or entering the preparation region, means (17, 18) are provided for measuring the condensation of the decontaminant gas on the surfaces of the enclosure and means (19) are provided for controlling the dispensing of the mixture of decontaminant gas and water vapour into the gas in the preparation region in response to the levels determined by said measuring to provide a predetermined level of condensation of the mixture of decontaminant gas and water vapour in the enclosure.

9. An apparatus as claimed in claim 8, further comprising means for circulating air through the preparation region and enclosure to convey the decontaminant gas/water vapour mixture to the enclosure.

10. An apparatus as claimed in claim 8, further comprising means for filtering the gas in said preparation region prior to circulation through the enclosure.

11. An apparatus as claimed in claim 8, further comprising:
means for monitoring the gas pressure in the enclosure; and
means for adjusting the gas pressure therein by controlling the supply of gas circulating through the enclosure.

12. An apparatus as claimed in claim 8, wherein the control means are arranged to terminate supply of the decontaminant gas and water vapour mixture in the preparation region after a sufficient amount of decontaminant gas has condensed in the enclosure to achieve decontamination and for removing the decontaminant gas from the enclosure.

13. An apparatus as claimed in claim 12, wherein the means for removing the decontaminant gas from the sealed enclosure comprises means for passing clean filtered gas through the enclosure and releasing the gas exiting the enclosure to atmosphere, or means for circulating the gas exiting the enclosure through an auxiliary circuit containing a catalytic decomposition device or absorption device for the decontaminant gas to remove the decontaminant gas.

14. A method of sterilising a sealed enclosure as claimed in claim 1, further comprising heating the gas in said preparation region prior to circulation through the enclosure.

15. An apparatus as claimed in claim 8, further comprising means for heating the gas in said preparation region prior to circulation through the enclosure.

16. A method as claimed in claim 1, wherein the condensation of the decontaminant gas on the surfaces of the enclosure is measured by a condensation sensor at least partially disposed within the enclosure.

17. An apparatus as claimed in claim 8, wherein the means for measuring the condensation of the decontaminant gas on the surfaces of the enclosure comprises a condensation sensor at least partially disposed within the enclosure.

* * * * *